(12) United States Patent
Walker

(10) Patent No.: US 11,337,367 B2
(45) Date of Patent: May 24, 2022

(54) PITCHFORK

(71) Applicant: Michael Kelly Walker, West Lafayette, IN (US)

(72) Inventor: Michael Kelly Walker, West Lafayette, IN (US)

( * ) Notice: Subject to any disclaimer, the term of this patent is extended or adjusted under 35 U.S.C. 154(b) by 0 days.

(21) Appl. No.: 16/415,368

(22) Filed: May 17, 2019

(65) Prior Publication Data
US 2019/0380264 A1 Dec. 19, 2019

Related U.S. Application Data

(60) Provisional application No. 62/644,517, filed on Mar. 18, 2018.

(51) Int. Cl.
*A01D 9/00* (2006.01)
*B62B 1/14* (2006.01)
*A61M 16/04* (2006.01)
*A63B 23/18* (2006.01)

(52) U.S. Cl.
CPC ........... *A01D 9/00* (2013.01); *A61M 16/0488* (2013.01); *A63B 23/18* (2013.01); *B62B 1/14* (2013.01); *A61M 2205/056* (2013.01); *A61M 2205/103* (2013.01); *A61M 2205/583* (2013.01); *A61M 2205/8275* (2013.01); *A61M 2210/0625* (2013.01); *A61M 2230/40* (2013.01)

(58) Field of Classification Search
CPC . A01D 9/00; A01D 9/02; A01D 11/02; A01D 11/04; A01D 11/06; A01B 1/028; B62B 1/147

USPC ........................................................ 294/55.5
See application file for complete search history.

(56) References Cited

U.S. PATENT DOCUMENTS

| | | | | |
|---|---|---|---|---|
| 567,391 A | * | 9/1896 | Hopper ................. | A01B 1/028 |
| | | | | 254/131.5 |
| 736,878 A | * | 8/1903 | Reis ........................ | A01D 7/00 |
| | | | | 56/400.04 |
| 1,935,841 A | * | 11/1933 | Fletcher ................. | B62B 1/147 |
| | | | | 298/2 |
| 1,998,524 A | * | 4/1935 | Roquet .................... | E01H 1/12 |
| | | | | 294/55.5 |
| 2,544,861 A | * | 3/1951 | Rath ....................... | A01D 7/00 |
| | | | | 56/400.14 |
| 2,638,730 A | * | 5/1953 | Davidson ............... | A01G 25/00 |
| | | | | 56/400.14 |
| 2,814,402 A | * | 11/1957 | Schaefer .................. | B62B 1/12 |
| | | | | 414/457 |
| 3,661,414 A | * | 5/1972 | Roth ...................... | B62B 1/147 |
| | | | | 294/59 |
| 5,799,998 A | * | 9/1998 | Gitterman, III ......... | A01K 1/01 |
| | | | | 294/51 |

(Continued)

*Primary Examiner* — Mark C Hageman
(74) *Attorney, Agent, or Firm* — Indiana University Maurer School of Law Intellectual Property Legal Clinic

(57) ABSTRACT

A pitchfork is disclosed. The pitchfork includes a pitchfork subassembly and a collection basket subassembly. The pitchfork subassembly includes a base, a plurality of tines coupled to the base, a handle receiving port coupled to the base, and a handle received in the handle receiving port. The collection basket subassembly includes two or more rear supports coupled to the base, a plurality of vertical wires coupled to the two or more rear supports, a plurality of horizontal wires coupled to the two or more rear supports, two or more side supports each coupled to an outside tine of the plurality of tines.

7 Claims, 4 Drawing Sheets

(56) References Cited

U.S. PATENT DOCUMENTS

| | | | | |
|---|---|---|---|---|
| 6,050,577 A | * | 4/2000 | Smith | A01D 87/127 |
| | | | | 280/47.24 |
| 6,059,515 A | * | 5/2000 | Keller | A01F 25/2036 |
| | | | | 280/47.131 |
| 8,262,145 B2 | * | 9/2012 | Berto | A01K 1/0114 |
| | | | | 209/417 |

* cited by examiner

PITCHFORK

RELATED APPLICATION

This application claims the benefit of U.S. Provisional Application No. 62/644,517 titled "Modified Pitchfolk" Updated Pitchfork," to Michael Walker et al., filed Mar. 18, 2018, the entire disclosures of which is expressly incorporated by reference herein.

TECHNICAL FIELD

The present disclosure generally relates to garden tools, and more particularly to a pitchfork.

BACKGROUND AND SUMMARY OF THE DISCLOSURE

This section introduces aspects that may help facilitate a better understanding of the disclosure. Accordingly, these statements are to be read in this light and are not to be understood as admissions about what is or is not prior art.

Lawn and garden tools are ubiquitous. Various tools in one form or another have been used for hundreds of years. However, improvements to these tools are made continuously, as evidenced by U.S. Pat. No. 5,626,009 to Bower et al., U.S. Pat. No. 8,955,893 to Stern et al., and U.S. Pat. No. 9,149,925 to Van Valin, each of which is incorporated by reference in its entirety into the present disclosure. In each of these improvements, the traditional tool has been improved to further achieve a stated goal. For example, in the U.S. Pat. No. 5,626,009 to Bower et al. a combination of a rack and hoe is provided by spreading the tines. In U.S. Pat. No. 8,955,893 to Stern et al., a combination of a bucket and a pitchfork is provided to scoop animal waste. In U.S. Pat. No. 9,149,925 to Van Valin, a combination of a handle and a pitchfork is provided to pick up debris in an ergonomic fashion.

In gathering debris including branches, brush trimmings, leaves, hay, and straw with a traditional pitchfork, a considerable amount of effort is required to maneuver the debris into a pile. As the pitchfork moves debris, along a surface, e.g., a grassy or uneven surface, either by vibration, or lack of cohesiveness, the debris separates from the pitchfork, requiring the operator to constantly go back over covered ground and collect the separated debris. This process will be repeated several times until all the debris is removed. To make this matter more complicated, the speed at which the pitchfork can be operated to gather debris is relatively slow, since by moving the pitchfork too fast, the aforementioned problem of separating debris becomes exacerbated.

According to one aspect of the present disclosure, a pitchfork is provided that comprises a pitchfork subassembly including a base and a plurality of tines coupled to the base. The pitchfork further comprises a handle coupled to the pitchfork subassembly and at least one wheel coupled to the pitchfork subassembly.

According to another aspect of the present disclosure, a pitchfork is provided that comprises a pitchfork subassembly including a base and a plurality of tines coupled to the base. The pitchfork further comprises a collection basket subassembly including at least two rear supports coupled to the base, a plurality of wires coupled to the at least two rear supports, and at least two side supports each coupled to an outside tine of the plurality of tines.

One aspect of the instant disclosure is related to a pitchfork comprising a pitchfork subassembly and a collection basket subassembly. The pitchfork subassembly includes a base and a plurality of tines coupled to the base. The collection basket subassembly includes at least two rear supports coupled to the base, a plurality of wires coupled to the at least two rear supports, and at least two rear supports each coupled to an outside tine of the plurality of tines. The pitchfork subassembly allows to pitchfork to bias debris into the collection basket subassembly. The rear supports, the wires, and the side supports form a basket that collects debris and prevent debris from leaving the pitchfork.

Another aspect of the instant disclosure is related to a pitchfork comprising a pitchfork and a collection basket device configured to retain loose items. The pitchfork subassembly comprises a base and a plurality of tines coupled to the base. The pitchfork subassembly allows to pitchfork to bias debris into the collection basket device which collects the debris.

BRIEF DESCRIPTION OF THE DRAWINGS

The previously described aspects of this disclosure will grow to be appreciated at a greater level once references to the following accompanying illustrations are expounded upon.

Figure 1:
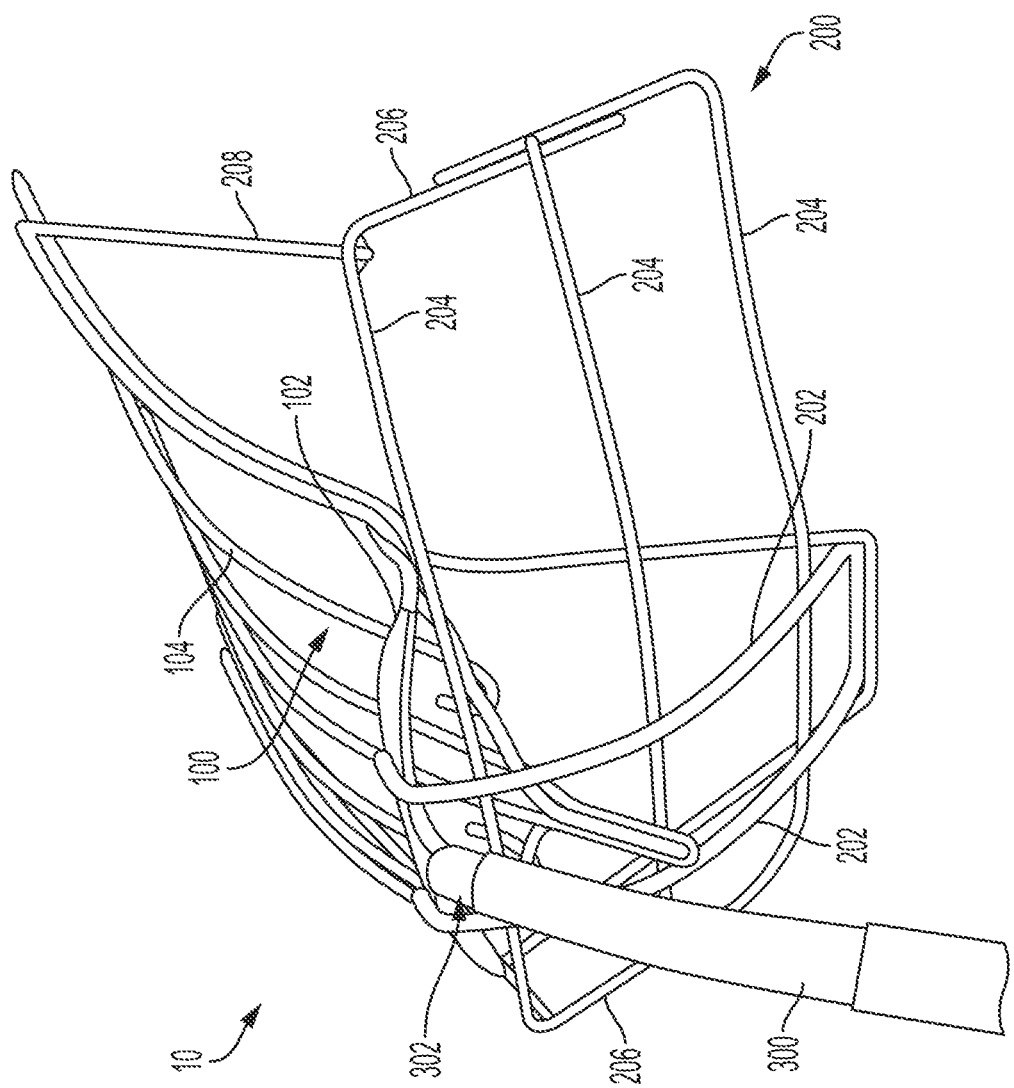
FIG. 1 is a rear perspective view of a pitchfork of the present disclosure.

The embodiments disclosed below are not intended to be exhaustive or limit the disclosure to the precise form disclosed in the following detailed description. Rather, the embodiments are chosen and described so that others skilled in the art may utilize their teachings. It will be understood that no limitation of the scope of the disclosure is thereby intended. The disclosure includes any alterations and further modifications in the illustrative devices and described methods and further applications of the principles of the disclosure which would normally occur to one skilled in the art to which the disclosure relates. Unless otherwise indicated, the components illustrated in the figures are shown in proportion to each other.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 2:
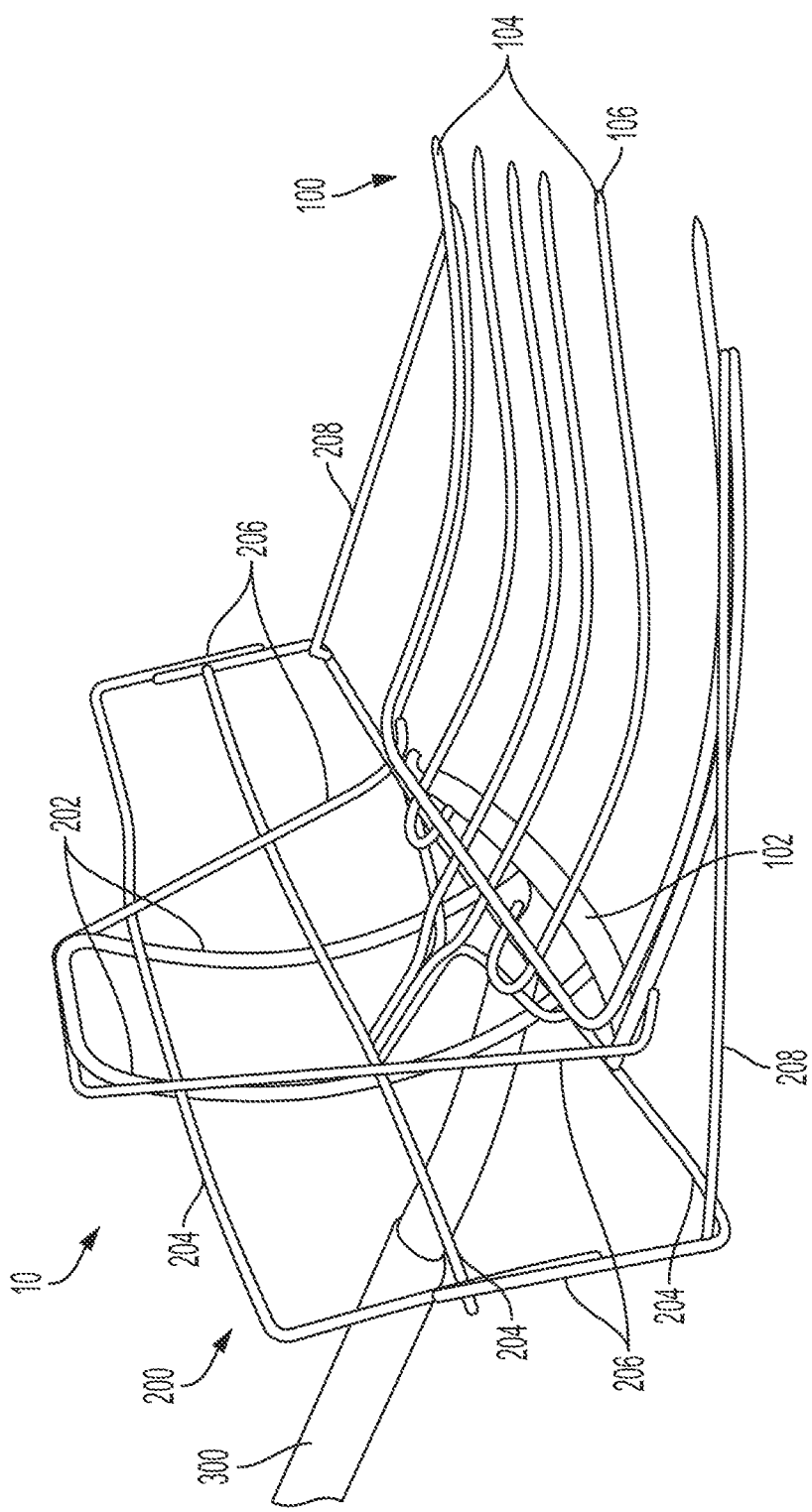
FIG. 2 is a side perspective of the pitchfork as shown in FIG. 1.
Figure 3:
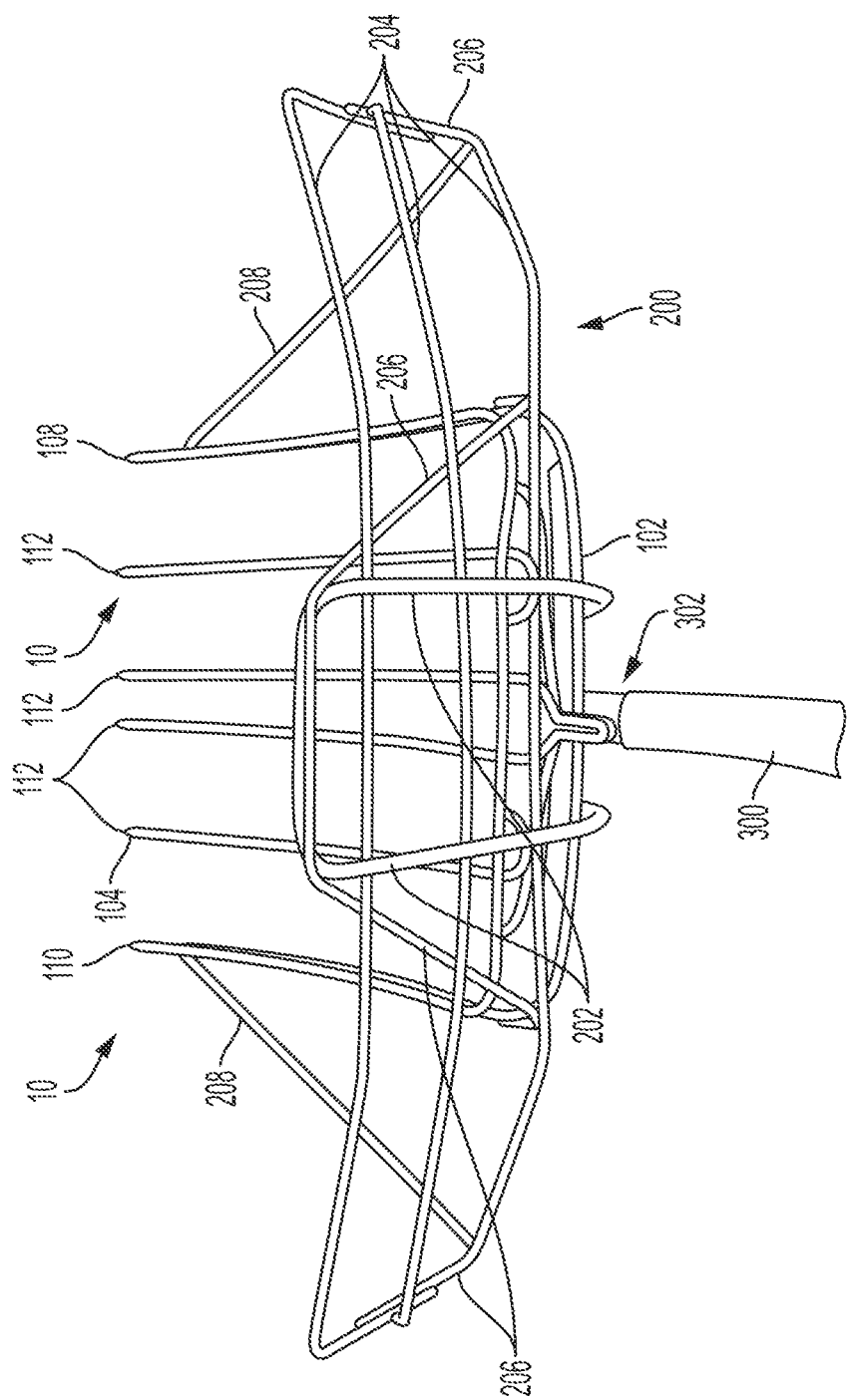
FIG. 3 is a rear perspective of the pitchfork as shown in FIG. 1.

A novel arrangement is described herein that allows collection of lawn, garden, and trash-like debris on smooth or uneven ground. Referring to FIGS. 1, 2, and 3, various views of a pitchfork 10 according to the present disclosure are provided. Pitchfork 10 includes two subassemblies, pitchfork subassembly 100 and collection basket subassembly 200 (also referred to as "catch-all"). Pitchfork subassembly 100 includes a base 102 and plurality of tines 104 extending from base 102. Tines 104 can number from at least two tines 104 to one hundred or more and are configured to provide a lifting functionality by being angularly disposed such that when tips 106 of tines 104 initially make contact with the debris to be collected, further movement of tines 104 in the same direction biases the debris to be moved from tips 106 of tines 104 toward base 102. Tines 104 and base 102 can be made from solid or tubular steel, hardened steel, galvanized steel, other metals known to a person having ordinary skill in the art, plastics, or a combination thereof. Plurality of times 104 includes a right-most tine 108, a left-most tine 110, and tines 112 positioned between right-most tine 108 and left most tine 110.

As mentioned above, pitchfork 10 also includes collection basket subassembly 200. Collection basket subassembly 200 is coupled to pitchfork assembly 100 by welding, fasteners, or formed as an integral apparatus with pitchfork assembly 100. The material of collection basket subassembly 200 can be selected from the group including solid or tubular steel, hardened steel, galvanized steel, plastics, and a combination thereof.

Collection basket subassembly 200 includes one or more rear supports 202, one or more horizontal wires 204, one or more vertical wires 206 (including two inner supports 206 and two outter supports 206 positioned outward of tow inner supports 206 as shown in FIG. 2), and side supports 208 as shown in FIGS. 1, 2, and 3. Rear supports 202 may couple to base 102 and form an angle with base 102. The combination of horizontal and vertical wires 204, 206 should be such that the spacing between wires 204, 206 generate substantially rectangular spaces so that when they come in contact with the debris provide a catching and gathering function, i.e., a basket function. Side supports 208 couples to corresponding tines 104 of pitchfork subassembly 100. Rear supports 202 and side supports 208 allows wires 204, 206 to be fixed on base 102.

The combination of vertical and horizontal wires 204, 206 generates a curved collection arrangement to encourage debris from disassociating and to stay within the envelope of collection basket subassembly 200. The curvature of collection basket subassembly 200 could be different for different embodiments. According to one embodiment, the extension of the collection basket subassembly from the outside tines can be from about 2 to about 20 inches and from about 5° to about 45°.

One or more of vertical wires 206 are secured to rear supports 202 by welding or fasteners. One or more of horizontal wires 204 are secured to rear support 202 by welding or fasteners.

Figure 4:
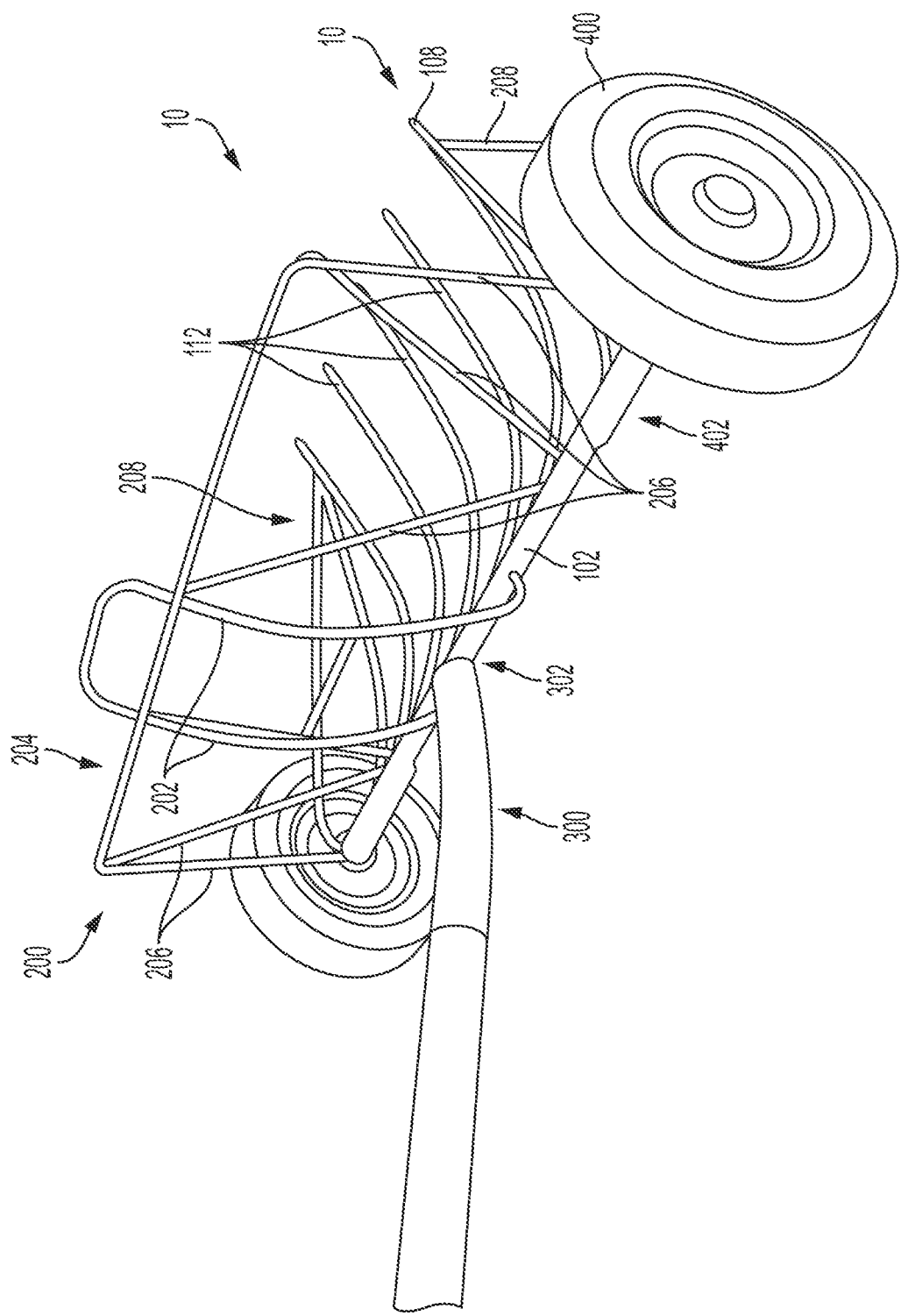
FIG. 4 is another rear perspective view of the pitchfork of FIG. 1 with wheels.

Base 102 is further coupled to a handle 300 by handle receiving port 302. Handle 300 is secured to base 102 via handle receiving port 302. Handle 300 is formed from wood, plastic, steel, or a combination thereof. As shown in FIG. 4, pithcfork 10 has a use orientation with handle 300 extending backwards.

According to one embodiment of the present disclosure, pitchfork 10 includes a pair of wheels 400 coupled to base 102 by an axle 402 that rotationally supports wheels 400. Rear supports 202 and side supports 208 are at least partially positioned between wheels 400. Side support 208, base 102, and tips 106 of tines 104 cooperate to define a keystone-shape with outer tines 104 defining narrower front corners of the keystone-shape and base 102 and side supports 208 cooperating to define broader rear corners of the keystone-shape. The rear corners are positioned between wheels 400.

Those having ordinary skill in the art will recognize that numerous modifications can be made to the specific implementations described above. The implementations should not be limited to the particular limitations described. Other implementations may be possible.

I claim:
1. A pitchfork comprising;
a pitchfork subassembly, including:
   a base, and
   a plurality of tines coupled to the base and including a right-most tine and a left-most tine positioned opposite to the right-most tine, the right-most tine and the left-most tine cooperating to define a tine width and being outside tines of the plurality of tines,
a collection basket subassembly, including:
   at least two rear supports coupled to the base,
   a plurality of wires coupled to the at least two rear supports, and
   at least two side supports each coupled to an at least one of the outside tines of the plurality of tines at a location, the collection basket having a basket width substantially wider than the tine width, a distance between the location and a tip of the outside tines is less than half a distance between the outside tines.
2. The pitchfork of claim 1, wherein
the plurality of tines defines a longitudinal axis equidistant between the right-most tine and the left-most tine, and
the pitchfork subassembly ftirther includes a handle receiving port coupled to the base and positioned along the longitudinal axis defined by the plurality of tines, further comprising:
   a handle received in the handle receiving port.
3. The pitchfork of claim 1, wherein the collection basket subassembly extends upwards from the base.
4. The pitchfork of claim 1, wherein the collection basket subassembly extends upwards from the plurality of tines.
5. The pitchfork of claim 1, wherein the side supports, base, and tips of the plurality of tines extend in a substantially horizontal direction when the handle is in a use orientation and cooperate to define a horizontal footprint having a keystone-shape.
6. The pitchfork of claim 1, wherein the collection basket subassembly further includes at least two inner supports coupled to the base, wherein the inner supports are longer than the rear supports.
7. The pitchfork of claim 6, wherein the inner supports have an upper-most portion that extends above upper-most portions of the rear supports when the plurality of tines are engaged with the ground.

* * * * *